(12) United States Patent
Duncan

(10) Patent No.: US 12,303,426 B2
(45) Date of Patent: May 20, 2025

(54) CARBON FIBER IMPREGNATED INFRARED GENERATING THERAPY CHAMBER FOR TARGETED TREATMENT OF THE BODY

(75) Inventor: Raleigh Duncan, Berkeley, CA (US)

(73) Assignee: SAUNA WORKS INC., Berkeley, CA (US)

( * ) Notice: Subject to any disclaimer, the term of this patent is extended or adjusted under 35 U.S.C. 154(b) by 0 days.

(21) Appl. No.: 13/464,588

(22) Filed: May 4, 2012

(65) Prior Publication Data

US 2012/0221080 A1 Aug. 30, 2012

Related U.S. Application Data

(63) Continuation of application No. 12/544,923, filed on Aug. 20, 2009, now abandoned.

(51) Int. Cl.
*A61F 7/00* (2006.01)
*A61H 33/06* (2006.01)
*A61N 5/06* (2006.01)

(52) U.S. Cl.
CPC ............ *A61F 7/007* (2013.01); *A61H 33/06* (2013.01); *A61N 5/06* (2013.01); *A61F 7/0053* (2013.01); *A61F 2007/0072* (2013.01); *A61F 2007/0088* (2013.01); *A61F 2007/0093* (2013.01); *A61F 2007/0096* (2013.01); *A61H 2201/5035* (2013.01); *A61H 2201/5064* (2013.01); *A61H 2201/5082* (2013.01); *A61H 2230/06* (2013.01); *A61N 2005/0636* (2013.01); *A61N 2005/0659* (2013.01); *A61N 2005/0668* (2013.01)

(58) Field of Classification Search
CPC ...... A61F 2007/0001–0052; A61F 2007/0077; A61F 2007/0086; A61F 2007/0088; A61F 2007/0093; A61F 2007/0095; A61F 7/007; A61F 7/0053; A61F 2007/005; A61F 2007/0096; H05B 1/0294; H05B 1/0275; H05B 1/0277; A61H 33/06
USPC .......................................................... 607/100
See application file for complete search history.

(56) References Cited

U.S. PATENT DOCUMENTS

| | | | | |
|---|---|---|---|---|
| 5,649,972 A | * | 7/1997 | Hochstein | 607/100 |
| 5,796,076 A | * | 8/1998 | Azuma | 219/486 |
| 5,897,804 A | * | 4/1999 | Hall | A61H 33/063 219/483 |
| 6,317,636 B1 | * | 11/2001 | Fujii | 607/100 |
| 6,745,411 B1 | * | 6/2004 | Kjonaas | A61H 33/063 4/524 |
| 6,814,889 B1 | * | 11/2004 | O'Grady | C08K 3/04 252/511 |

(Continued)

FOREIGN PATENT DOCUMENTS

CN 200820159505 * 11/2008
CN 201320352 Y * 10/2009

OTHER PUBLICATIONS

Machine Translation of Description for CN-201320352-Y (2020).*

*Primary Examiner* — Ronald Hupczey, Jr.
(74) *Attorney, Agent, or Firm* — Kwan & Olynick LLP

(57) ABSTRACT

A therapeutic chamber controls the targeted application of infrared radiation according to programs tailored to conditions or areas of the body in need of treatment. Programs are provided and may also be determined or designed by a treatment administrator or subject. An embodiment utilizes groups of carbon fiber impregnated infrared generating sheets to provide targeted radiation in an energy efficient fashion.

5 Claims, 4 Drawing Sheets

(56) References Cited

U.S. PATENT DOCUMENTS

| | | | |
|---|---|---|---|
| 6,965,097 B2* | 11/2005 | Lee | 219/492 |
| 7,108,712 B2* | 9/2006 | Barghelame | A61H 33/06 |
| | | | 607/88 |
| 7,194,198 B2* | 3/2007 | Lee | F24C 7/043 |
| | | | 219/544 |
| 2001/0003216 A1* | 6/2001 | Komulainen | A62C 37/46 |
| | | | 4/524 |
| 2002/0183814 A1* | 12/2002 | Ono | 607/100 |
| 2003/0155347 A1* | 8/2003 | Oh | H05B 3/34 |
| | | | 219/545 |
| 2005/0021114 A1* | 1/2005 | Hidaka | A47C 7/748 |
| | | | 607/112 |
| 2005/0215926 A1* | 9/2005 | Thrasher | 601/70 |
| 2005/0286877 A1* | 12/2005 | Chen | A61H 33/063 |
| | | | 392/416 |
| 2007/0033069 A1* | 2/2007 | Rao et al. | 705/2 |
| 2007/0198004 A1* | 8/2007 | Altshuler et al. | 606/9 |
| 2007/0294818 A1* | 12/2007 | Tei | A61H 33/063 |
| | | | 4/524 |
| 2008/0046044 A1* | 2/2008 | Jahnigen et al. | 607/100 |
| 2010/0017953 A1* | 1/2010 | O'Keeffe | A61H 33/063 |
| | | | 4/524 |

\* cited by examiner

CARBON FIBER IMPREGNATED INFRARED GENERATING THERAPY CHAMBER FOR TARGETED TREATMENT OF THE BODY

CROSS-REFERENCE TO RELATED APPLICATIONS

This application is a Continuation of U.S. patent application Ser. No. 12/544,923, filed Aug. 20, 2009, and entitled INFRARED THERAPY CHAMBER. This application is incorporated herein by reference in its entirety.

BACKGROUND OF THE INVENTION

Some of the benefits of hot baths and chambers, including saunas, have been known for years. However, even recent incarnations with modern control systems essentially mimic the centuries old technique of providing a hot room. The vast majority of prior saunas use a (metal alloy or ceramic etc) resistance type heating coil or element. While some existing saunas utilize infrared generating coils or elements, with both types of saunas a set point temperature is maintained with a very simple control device that typically measures the overall air or heater temperature and regulates the set point accordingly.

SUMMARY OF THE INVENTION

A therapeutic chamber controls the targeted application of infrared radiation according to programs tailored to conditions or areas of the body in need of treatment. Programs are provided and may also be determined or designed by a treatment administrator or subject. An embodiment utilizes groups of carbon fiber impregnated infrared generating sheets to provide targeted radiation in an energy efficient fashion.

One aspect relates to a treatment chamber that comprises a subject treatment area, a control module, a subject detection sensor, and a plurality of carbon fiber impregnated infrared generating (CFIG) sheets, each of the plurality of sheets having a principal plane and generating infrared radiation substantially perpendicular to the principal plane. A first CFIG sheet of the plurality is positioned adjacent a left side of the subject, providing infrared radiation substantially perpendicular to a left side of the subject. A second CFIG sheet of the plurality is positioned adjacent a back of the subject, providing infrared radiation substantially perpendicular to the back of the subject. A third CFIG sheet of the plurality is positioned adjacent a right side of the subject, providing infrared radiation substantially perpendicular to a right side of the subject. The control module is configured to treat the left portion of the subject by activating the first CFIG sheet for a first period of time while the second CFIG sheet is also activated, and deactivate one of the first or second sheets for a second period while the other of the sheets remains activated, activate both the first and third sheets for a third period, and activate the other of the sheets in a fourth period that was not activated during the second period.

Another aspect related to a therapeutic method. The method comprises (a) providing a chamber comprising a subject treatment area, a control module comprising a user interface and control logic, and a plurality of infrared generating elements; (b) causing, with the control logic of the control module, vasodilation at a targeted region of a subject in the subject treatment area by activating an infrared generating element of the plurality; (c) causing, with control logic of the control module, vasoconstriction after said vasodilation; and (d) repeating steps (b) and (c) causing a pumping effect through repeated vasodilation and vasoconstriction.

Another aspect relates to a chamber comprising a subject treatment area, a control module comprising a user interface module and control logic, and an infrared generating element. The control module is configured to allow a person to enter a desired wavelength at the user interface, and activate at least one of the plurality of planar infrared heaters to produce infrared radiation at the desired wavelength. A person may also enter a material to be targeted by the chamber, such as a human body, or hot rocks or other massage implements, and reference a memory of the control module to determine a wavelength that is optimal for heating the targeted material. It is to be understood that the temperature of the heaters is dependent on their wavelength.

A further understanding of the nature and advantages of the present invention may be realized by reference to the remaining portions of the specification and the drawings.

DETAILED DESCRIPTION OF THE PREFERRED EMBODIMENTS

Reference will now be made in detail to specific embodiments of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is' intended to cover alternatives, modifications, and equivalents as may be included within the spirit and scope of the invention as defined by the appended claims. In the following description, specific details are set forth in order to provide a thorough understanding of the present invention. The present invention may be practiced without some or all of these specific details. In addition, well known features may not have been described in detail to avoid unnecessarily obscuring the invention.

Infrared ("IR") treatment chambers in accordance with the present invention have multiple zones each individually controlled to deliver infrared radiation according to a procedure tailored to produce a desired result. This may include specific modulation sequences tailored to address specific conditions.

In certain embodiments, individual parts of the body or conditions are individually treated according to specific radiation sequences. The sequences may involve multiple different sources producing different frequencies and amplitudes of radiation delivered from various angles.

Infrared radiation in a controlled delivery system has the potential for wound healing, detoxification, pain relief, increasing metabolism, and stress reduction through increase of parasympathetic stimulation.

Preferred embodiments utilize a planar ultra thin IR radiating element (about 1/16") with a sheet of carbon fiber impregnated paper that dispense a uniform pattern of infrared radiation in a direction substantially orthogonal to the plane of the element. Such a carbon fiber impregnated infrared generating ("CFIG") sheet has the advantage of having a low magnetic field while at the same time producing a large amount of infrared spectrum radiation with low energy consumption. In certain embodiments, the energy consumption can be one third as much as prior systems with conventional metallic resistance heaters. This also translates in certain embodiments into chambers that can run on 110 volt AC current and be conveniently plugged into a readily available 15 ampere circuit. Therefore, in numerous applications, no electrical (wiring) infrastructure modifications need be made to accommodate the chamber in a location with commonly available 110V 15A circuits.

Figure 1:
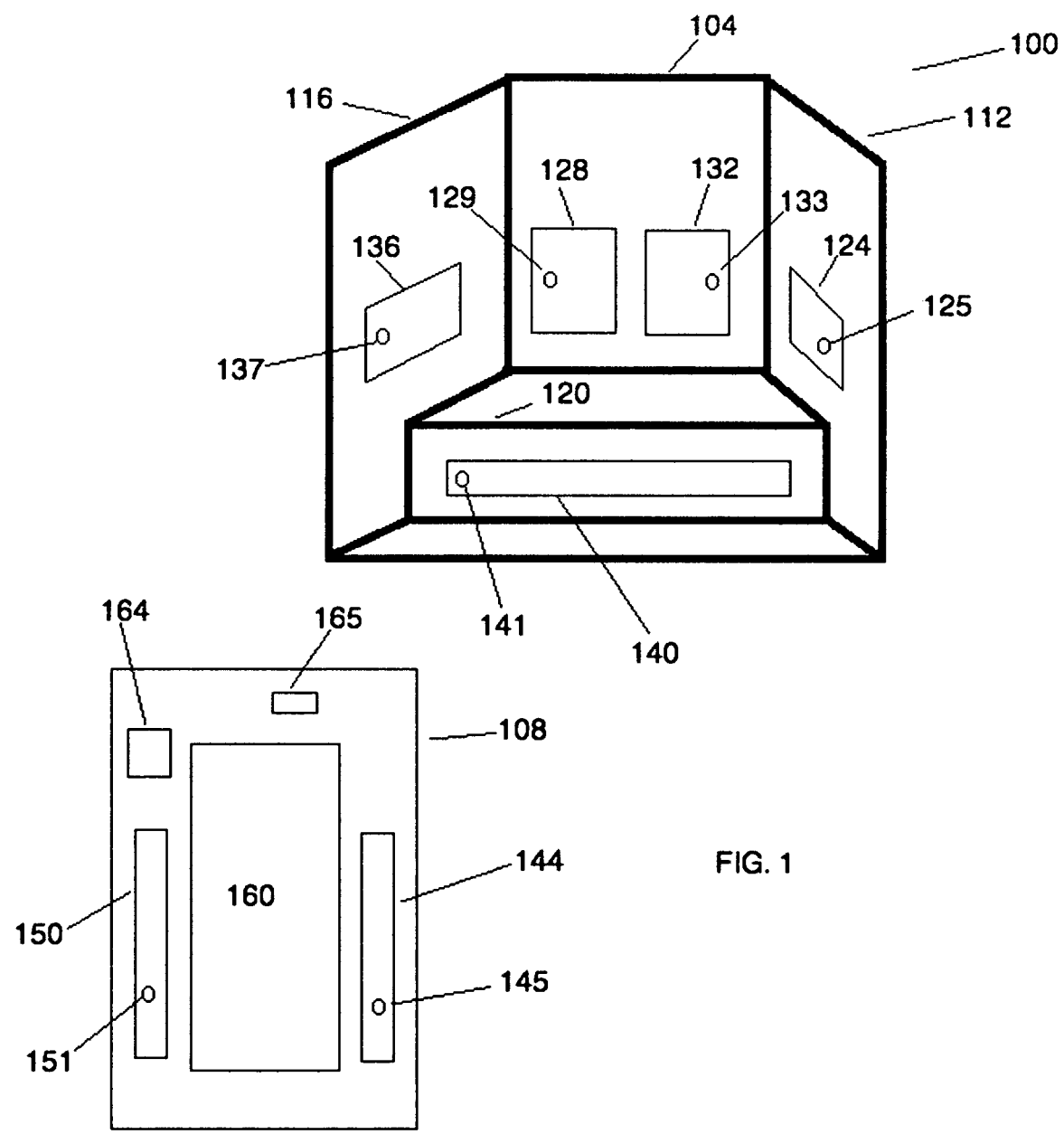
FIG. 1 is a perspective diagram of chamber 100, according to an embodiment of the invention.

FIG. 1 illustrates treatment chamber 100. Chamber 100 has an outer enclosure comprising front wall 108 with door 160, right side wall 116, left side wall 112, and rear wall 104. Chamber 100 further comprises a bench 120. When a subject is situated upon bench 120 the subject's right side will be adjacent right side wall 116, whereas the subject's left side will be adjacent left side wall 112.

The embodiment of chamber 100 shown in FIG. 1 employs numerous CFIG sheets. CFIG sheet 140 is placed below the bench and generates infrared radiation that is applied to the subject's legs. CFIG sheet 136 is upon left wall 116 and adjacent the subject's right side and shoulder. CFIG sheet 124 is situated upon the left wall 112 and is adjacent the subject's left side and shoulder. One or more CFIG sheets may be upon the rear wall. FIG. 1 illustrates two CFIG sheets, left rear CFIG sheet 132 and right rear CFIG sheet 128. CFIG sheets 150 and 144 are upon front wall 108. An additional CFIG sheet may be placed up on door 160.

Subject sensor 122 detects the presence of the subject within the chamber. Sensor 122 is preferably a motion detecting sensor, but may be another type. For example a sensor that detects the opening or closing of door 160 or the subject sitting upon the bench may also be used to activate and deactivate various components. Motion detection sensors may detect reflectance of a transmitted signal back to a co-located emitter/collector or may detect interruption between an emitter and a collector. Control unit 164 incorporates a user interface and the logic that controls the chamber. Air temperature sensor 165 is used to measure the ambient temperature within the chamber. Attached to or incorporated with the structure of each of the CFIG sheets is a sensor to measure the temperature and/or radiation wavelength of each CFIG sheet: sensor 141 at CFIG sheet 140; sensor 125 at CFIG sheet 124; sensor 133 at CFIG sheet 132; sensor 129 at CFIG sheet 128; sensor 137 at CFIG sheet 136; sensor 145 at CFIG sheet 144; and sensor 151 at CFIG sheet 150.

A power supply and other switching circuitry (not shown) is below bench 120 or in another suitable location.

Figure 4:
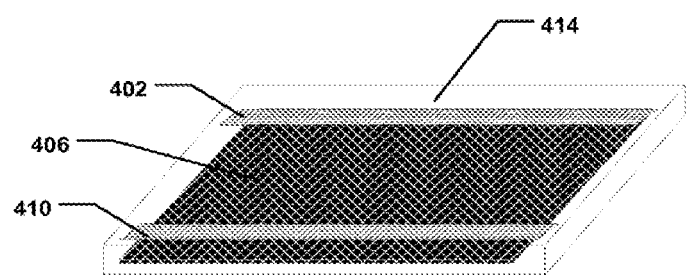
FIG. 4 is a perspective view of a carbon fiber impregnated infrared generating sheet, according to an embodiment of the invention.

FIG. 4 is a perspective view of a CFIG sheet, according to an embodiment of the invention. The CFIG sheets have microscopic carbon fibers approximately 0.000004" in diameter as a resistive and emissive source sandwiched between pre'-impregnated epoxy fiber cloth, an insulative fiber layer, all depicted as 406 and outer layers 414, for example polyethylene terephtalate film. In some embodiments of the CFIG sheets, the carbon fibers are interlaced with microscopic ceramic particles, and compressed under temperature and pressure until a sufficient seal is created to encapsulate the composite structure. The current flows from anode 402 to cathode 410 conductive (e.g.) metallic strips also encapsulated in the matrix, connected to the carbon fibers. The diameter of the carbon fibers are varied between the anode and cathode to create the desired wattage. The density of the carbon fibers may also be varied to create different radiating zones in one sheet. For example, one sheet may have multiple regions with different fiber density in order to produce a wide spectrum of infrared radiation. For example, a region with a first density would produce a first spectrum and a region with a second density would produce a second spectrum etc. Alternatively the density may be linearly increased within one region.

A conventional resistance element heater may also be included within chamber 100 in certain embodiments. Such heaters can be made of metal with resistive wire, ceramic with resistive wire heating element, quartz lamps, or incandescent lamps.

Metal/ceramic/halogen heaters that employ closed loop feedback sensors or arrayed individual temperature sensors and have full spectrum heat capacity may also be employed. Embodiments of such a heater preferably have a heating rod and reflector, and a tapered ceramic secondary heating element, either perforated or not. The tapering and position of the secondary (in certain cases passive) element result in a heat profile that varies at different areas of the heater.

Figure 2:
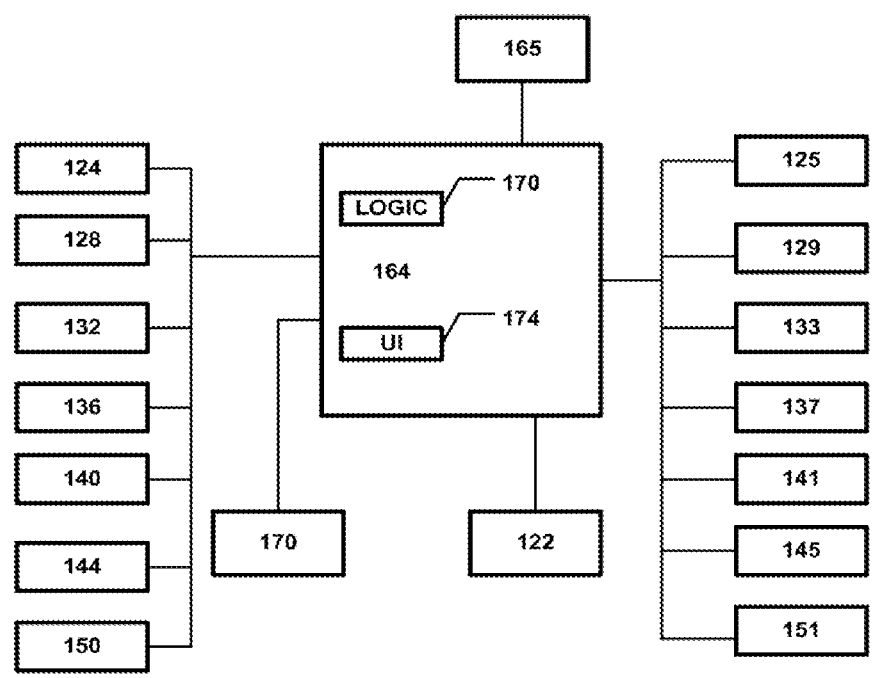
FIG. 2 is a block diagram of some components of chamber 100.

As seen in FIG. 2, control unit 164 comprises logic 170 and user interface unit 174. In certain embodiments control unit 164 is a programmable logic controller, whereas in other embodiments it may be a more powerful computing device, including a conventional microprocessor. Control unit 164 is coupled to air temperature sensor 165, subject sensor 122 and heart rate monitor 170. Control unit 164 is also coupled to the various CFIG sheet sensors 125, 129, 133, 137, 141, 145 and 151 etc, and the CFIG sheets 124, 128, 132, 136, 140, 144, and 150. For the sake of simplicity, the connection to the power supply and various circuitry and such as relays and triacs that may be used to power high power devices such as the CFIG sheets and a conventional heater, if present, are not shown. The control unit user interface may comprise an LED panel and/or LCD screen, buttons for on/off, temp, time, and readout time/temp on the LCD/LED screen.

Figure 3:
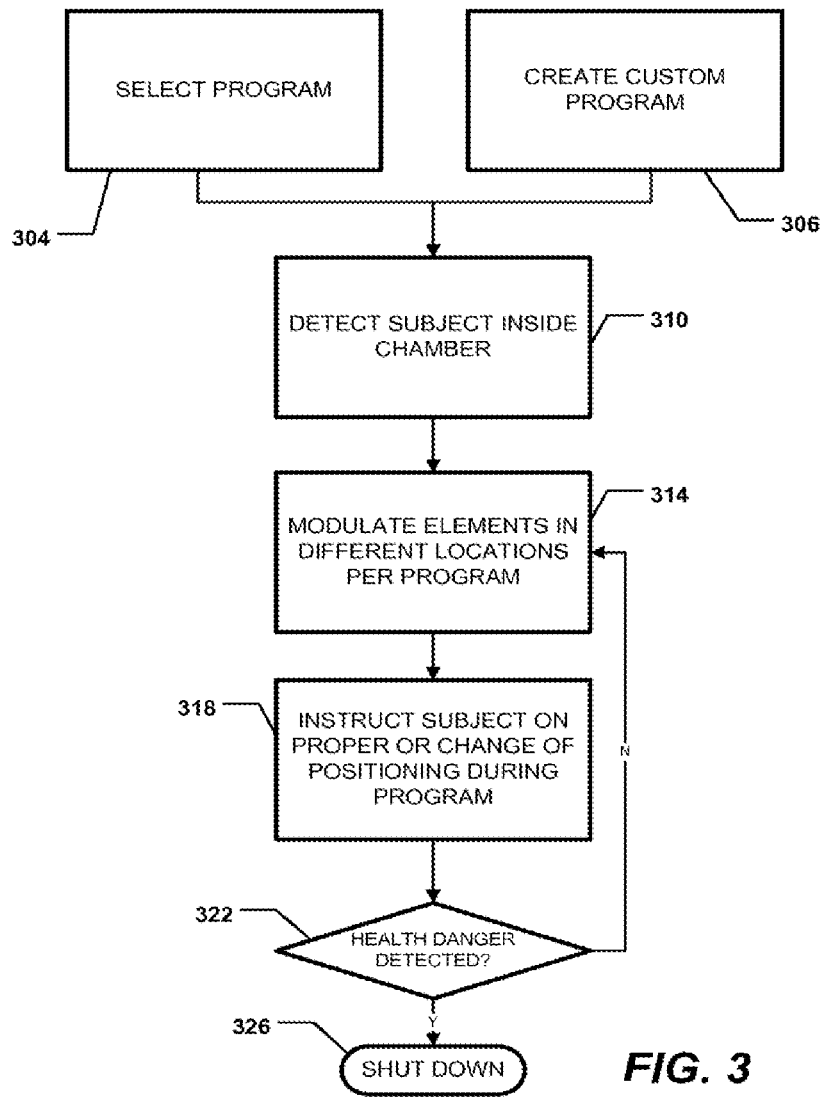
FIG. 3 is a flow chart illustrating operation of a chamber, according to an embodiment of the invention.

FIG. 3 is a flowchart of operation and use of chamber 100. In step 304 an administrator or subject selects a program. Alternatively the administrator or subject creates a custom program in step 306. In step 310, the presence of the subject inside the chamber is optionally detected. This is useful in scenarios where the subject is alone and the chamber is set to activate upon detecting presence or entry. The control unit motion detector senses the presence of a moving body within the enclosure. This feature results in energy savings as the system can stay in a lower pre-warm mode until a body gets into the sauna, at which point the sauna senses the body and brings the heaters up to a higher temperature to facilitate the desired effect. The sensors can also be used in larger saunas (up to 30 person) to turn on certain "zones" when a body(ies) is/are detected. The sauna air temperature may be kept warm prior to motion sensor activation by use of an air temperature sensor keeping the sauna at a preset temperature of between 50 F and 120 F so that the sauna interior is slightly warm to mildly hot depending on user preference. Infrared technology lends itself to this energy saving innovation because the infrared used in this sauna application primarily heats the body and not the air. There is little need to keep the sauna and all its heaters on full bore waiting for someone to enter the sauna as is the case with the traditional Finnish sauna. The motion detector turns on the appropriate heater zones. The CFIG sheets used in certain embodiments have a quick response time, so a direct energy savings is realized.

In step 314, the control module modulates the (CFIG) elements at different locations according to the program. In step 318, the control module generates instructions to the administrator and/or subject on proper positioning during the program. For example, at a stage of the program the subject may be instructed to position the right shoulder at the right heater, or to elevate an arm or otherwise move or reposition the body or body part. As another example, the administrator or subject may be instructed to "keep door open throughout session."

In step 322, the control module monitors whether a health danger is detected. For example, this may be determined with heart rate monitor 170 if a heart rate is above a threshold determined appropriate for a given cycle and age/condition of the subject, a danger may be indicated. As another example, an unacceptable change in the rate of the heart may also indicate a danger, as may an unacceptably low heart rate. In embodiments blood pressure measurement may be available, and an unacceptable blood pressure measurement may also indicate a health danger. When such a danger is detected, the control module will shut down the elements 326 and may also notify the subject of the danger and to exit the chamber.

The current state of the art in infrared saunas normally employs a plc control and power supply with a temperature probe that turns all heaters on and off responding to a digitally preset air temperature reading. The sauna then shuts off after the digital timer.

Embodiments modulate the infrared radiation in a dynamic programmable fashion so that each zone is individually programmed and therapeutic benefits can be orchestrated in sequences that exact the maximum benefit from the system and to the body.

In addition to pre-programmed sequences, treatment administrator or user designed sequences may also be employed.

Discrete individual programs can be designed by the administrator to modulate individual radiating element outputs. Certain areas of the body can be targeted with a desired radiation or heat level for a preset period of time or, for a global effect, with changing temperatures and zones over time.

In certain embodiments, the wavelength produced by the infrared generating elements is ramped up or down in a linear or non linear fashion. The rate of change of the wavelength over time (DDt) may also be controlled in a linear or non linear fashion.

Programs may be tailored to specific body regions or body parts. One program, for example, allows heat to be increased to a CFIG sheet sensor temperature of 250 degrees Fahrenheit at the location of the right shoulder. This program would allow the specific CFIG sheet (i.e. back and right side sheets 128 and 136 respectively) in that area to be activated around the right shoulder. The other CFIG sheets may be set to a lower setting than CFIG sheets 128 and 136 in this example, or may alternatively be switched off.

The IR radiation would be directed for five minutes to the area, causing vasodilation, which in turns brings oxygenated blood to the specific area (e.g. shoulder). The radiating elements would then be shut off or set a minimal setting for a period of time, e.g. two minutes. This causes the vasodilation of the blood vessels to decrease (vasoconstriction), having the effect of "pumping out" lymph fluid and other accumulated "waste material." One or more of the radiating elements are then turned back on to 250 degrees Fahrenheit or a wavelength of about 7-'8 (e.g. 7.4) microns penetrating to a depth of 25 millimeters to facilitate targeted localized vasodilation for another five minutes and then the cycle repeats for a number of cycles or for an overall duration, for example 20-60 minutes.

The overall effect of this program will allow for pain reduction, increased healing and reduced inflammation. During the shoulder program the other remaining heaters maintain a warm temperature in the chamber to allow the patient/user to relax as the body is brought into systemic parasympathetic mode through applied lower heat (150 degrees Fahrenheit CFIG temperature).

Other cycles employed by the chamber include a cardiovascular targeted system of modulation. The cardiovascular system modulates the various elements to result in maximum cardiovascular benefits. This is a type of passive cardio workout and is obtained by reaching the lower range of target heart rate levels, for example those set by the AHA. For example the target heart rates for a 40 year old male are 90 beats per minute to 153 beats per minute. These values represent 50 to 80% of the maximum heart rate for this subject, 180 beats per minute. The subjects using this subroutine can expect to raise their heart rate from 10 to 25% from resting heart rate. The cardiovascular routine utilizes maximum output of all CFIG sheets for a period, e.g. for ten to fifteen minutes and then no or minimal output for another period of e.g. four to seven minutes, then back up to maximum output for another period, e.g. four to seven minutes highest heat, and then again another period of no or minimal output for e.g. four to seven minutes. These described cycles may be repeated as desired.

Tests have shown that such a controlled increase in heart rate (passive aerobic workout) is beneficial for all persons, especially those that find traditional exercise difficult, such as the elderly or disabled. This program administers this workout safely and efficiently allowing the body to "acclimate and rest" in the intervals allowing maximum aerobic benefit safely and efficiently. During a 20 to 60 minute session a program may change heater temperature(s), heater location, time interval over 100 times as needed for the therapeutic effect desired. Doctors and licensed physical therapists will be able to utilize these routines to treat various musculoskeletal conditions.

Infrared Cellular Resonance in Application to Heavy Metal Detoxification

There is a growing body of research theorizing that the infrared wavelength is useful in detoxifying the body from heavy metals such as mercury and cadmium, as well as many other harmful substances. In particular, wavelengths between 6 and 9.5 microns are thought to be particularly effective as such wavelengths resonate the heavy metals at a frequency appropriate to cleave the heavy metal from the adjacent cell or tissue. The IR output of the CFIG sheets can be adjusted to create IR radiation at an appropriate wavelength to resonate a selected material and cleave it from a particular type of tissue. As an example, the therapeutic micron range for heavy metal detox is approximately 9.5 microns down to 6.0 microns.

The functions of this advanced infrared sauna system are managed by the controller programs/logic stored in a memory of the controller. As mentioned, the controller senses and modulates the various elements of the system in a closed loop feedback system.

Exemplary Programs/Routines

The routines listed below are current programs and do not reflect all possible therapeutic combinations. The open architecture and programmability allow programs to be added and customized for specific needs and effects as required. (All temperatures reflect heater surface temperature in Fahrenheit unless otherwise noted.)

1. Standard Program—on for 60 minutes. All 4 heaters @ 200 F
2. Cardio—45 minute program, initiated by motion sensor:
   15 min. warm-up—beep
   all heaters 250 F for 10 minutes
   all heaters 150 F for 5 minutes
   all heaters 250 F for 10 minutes
   all heaters 150 F for 5 minutes
   all heaters 250 F for 10 minutes
   all heaters 150 F for 5 minutes
3. Derma health—45 minute program, initiated by motion sensor:
   all heaters maximum 190 F for 10 minutes
   all heaters minimum 150 F for 20 min
   all heaters max 170 F for 10 min
   all heaters min 190 F for 5 min
4. Stress reduction—1 hour program:
   maximum temp 15 minute warm up, program waits for human detection
   all heaters 150 F for 15 min
   all heaters 190 F for 15 min
   all heaters 220 F for 15 min
5. Pre exercise warm up, initiated by motion sensor:
   15 min low warm up 200 F, program waits for human detection
   20 min 230 F
6. Post exercise warm down, initiated by motion sensor:
   no warm up
   10 minutes 190 F all heaters
   10 minutes 150 F
   10 minutes 170 F
7. Joint health:
   warm up max 200 F, program waits for human detection
   heaters 1, 2, 3 @ 240 F for 30 minutes
8. Meditation, initiated by motion sensor:
   keeps cabin warm; air temperature to 82 F
9. Corporal relaxation:
   min warm up at 200 F, program waits for human detection
   30 minutes 230 F
10. Water detox:
    warm up 240 F highest program waits for human detection
    30 minutes 230 F
11. Oil detox:
    door open for 1st 15 minutes, all heaters 280 F
    door closed for 30 min 150 F
12. Heavy metal detox:
    door open entire session all heaters alternate in cascading range for two-minute intervals between ISOF and 200 F for 20 minutes. This allows for all desirable micron wavelengths for cellular resonance vibration phenomenon
    all heaters on low; 160 F for 10 minutes, allows flushing of toxins
13. Energy savings:
    five minute warm-up; program waits for human detection
    front, side, back heaters on 160 F
14. Micron specific:
    Heaters can be set to specific wavelength (e.g. in microns) range of infrared. The micron selection will be made at the keypad and the sensors will measure the wavelength or a variable related to the wavelength. The program may then wait for human detection before activating the CFIG sheets.
    *Program Runs Heaters at Preset Micron Level for Preset Time
15. Front heater only, variable temp/micron, program waits for human detection
16. Side left heater only, variable temp/micron, program waits for human detection
17. Side right heater only, variable temp/micron, program waits for human detection
18. Right shoulder program (prewarm cabin 150 F front heaters), program waits for human detection:
    side right heater and back heater 250 F for 5 minutes
    all heaters off for 2 minutes
    side right heater and back heater 250 F for 5 minutes
    all heaters off for 2 minutes
    side right heater and back heater 250 F for 5 minutes
    all heaters off for 2 minutes
    side right heater and back heater 250 F for 5 minutes
    all heaters off for 2 minutes
    side right heater and back heater 250 F for 5 minutes
    all heaters off for 2 minutes
19. Left shoulder program (prewarm cabin 150 F front heaters), program waits for human detection:
    side left heater and back heater 250 F for 5 minutes
    all heaters off for 2 minutes
    side right heater and back heater 250 F for 5 minutes
    all heaters off for 2 minutes
    side right heater and back heater 250 F for 5 minutes
    all heaters off for 2 minutes
    side left heater and back heater 250 F for 5 minutes
    all heaters off for 2 minutes
    side left heater and back heater 250 F for 5 minutes
    all heaters off for 2 minutes
20. Lower extremity edema pump (prewarm cabin 150 F front heaters), program waits for human detection:
    front heater and bottom heater 250 F for 5 minutes
    all heaters off for 2 minutes
    front heater and bottom heater 250 F for 5 minutes
    all heaters off for 2 minutes
    front heater and bottom heater 250 F for 5 minutes
    all heaters off for 2 minutes
    front heater and bottom heater 250 F for 5 minutes
    all heaters off for 2 minutes
    front heater and bottom heater 250 F for 5 minutes
    all heaters off for 2 minutes While the invention has been particularly shown and described with reference to specific embodiments thereof, it will be understood by those skilled in the art that changes in the form and details of the disclosed embodiments may be made without departing from the spirit or scope of the invention.

In addition, although various advantages, aspects, and objects of the present invention have been discussed herein with reference to various embodiments, it will be understood that the scope of the invention should not be limited by reference to such advantages, aspects, and objects. Rather, the scope of the invention should be determined with reference to the appended claims.

What is claimed is:

1. A treatment chamber comprising:
   a subject treatment area, said subject treatment area including a floor, at least a first wall, and a seat;
   a planar infrared heater attached to the first wall, the planar infrared heater being a carbon fiber impregnated infrared generating (CFIG) paper sheet having a plurality of microscopic carbon fibers approximately 0.000004 inches in diameter as a resistive and emissive source sandwiched between pre-impregnated epoxy fiber cloth, wherein the density of carbon fibers is varied to create different radiating zones in the sheet, wherein the sheet includes multiple regions with different fiber density in order to produce a wide spectrum of infrared radiation;
   an air temperature sensor configured to measure temperature;
   a wavelength sensor separate from the air temperature sensor, the wavelength sensor configured to measure a wavelength of infrared radiation produced by the planar infrared heater; and
   a control module comprising a user interface module and control logic enabling an operator of the chamber to select and activate a stored treatment program that is configured to implement one or more predetermined operating sequences to activate or deactivate the planar infrared heater.

2. The treatment chamber of claim 1, wherein the control module is further configured to monitor a signal from a subject detection sensor and to activate the control module user interface upon detection of motion at the chamber.

3. The treatment chamber of claim 1, further comprising a heart rate sensor, and wherein the control module is further configured to adjust the amount of infrared radiation produced by the planar heater in response to a change in the subject heart rate as detected by the heart rate sensor, and wherein the control module is further configured to shut off the infrared radiation entirely if the heart rate detected indicates a danger to the subject's health.

4. The treatment chamber of claim 1, wherein a first region of the sheet with a first fiber density produces a first spectrum of infrared radiation and a second region with a second fiber density products a second spectrum of infrared radiation.

5. The treatment chamber of claim 1, wherein the fiber density is linearly increased within a region of the sheet.

* * * * *